(12) United States Patent
Crane et al.

(10) Patent No.: US 7,925,332 B2
(45) Date of Patent: Apr. 12, 2011

(54) DISPOSABLE LIGHT SOURCE PATCH FOR ENHANCED VISUALIZATION OF SUBCUTANEOUS STRUCTURES

(75) Inventors: Robert L. Crane, Dayton, OH (US); James E. McGuire, Jr., Columbus, OH (US); David M. Callard, Palo Alto, CA (US)

(73) Assignees: Infrared Imaging Systems, Inc., Columbus, OH (US); The United States of America as represented by the Secretary of the Air Force, Washington, DC (US)

( * ) Notice: Subject to any disclaimer, the term of this patent is extended or adjusted under 35 U.S.C. 154(b) by 915 days.

(21) Appl. No.: 11/382,736

(22) Filed: May 11, 2006

(65) Prior Publication Data
US 2007/0032721 A1 Feb. 8, 2007

Related U.S. Application Data

(60) Provisional application No. 60/680,600, filed on May 13, 2005.

(51) Int. Cl.
*A61B 6/00* (2006.01)
*A61B 5/00* (2006.01)
(52) U.S. Cl. .......................... 600/476; 600/344
(58) Field of Classification Search ................ 600/362
See application file for complete search history.

(56) References Cited

U.S. PATENT DOCUMENTS

| | | | |
|---|---|---|---|
| 4,817,622 A | 4/1989 | Pennypacker et al. | |
| 5,241,170 A | 8/1993 | Field, Jr. et al. | |
| 5,417,688 A | 5/1995 | Elstrom et al. | |
| 5,519,208 A | 5/1996 | Esparza et al. | |
| 5,817,012 A * | 10/1998 | Schoendorfer | 600/362 |
| 5,830,136 A * | 11/1998 | Delonzor et al. | 600/323 |
| 6,032,070 A | 2/2000 | Flock et al. | |
| 6,230,046 B1 * | 5/2001 | Crane et al. | 600/476 |
| 6,272,374 B1 | 8/2001 | Flock et al. | |
| 6,556,858 B1 | 4/2003 | Zeman | |
| 6,745,061 B1 * | 6/2004 | Hicks et al. | 600/344 |
| 6,748,254 B2 * | 6/2004 | Chin et al. | 600/344 |
| 6,993,167 B1 * | 1/2006 | Skladnev et al. | 382/128 |
| 7,190,986 B1 * | 3/2007 | Hannula et al. | 600/344 |
| 2003/0032950 A1 * | 2/2003 | Altshuler et al. | 606/9 |
| 2003/0130575 A1 * | 7/2003 | Desai | 600/417 |
| 2004/0215081 A1 | 10/2004 | Crane et al. | |
| 2005/0228260 A1 * | 10/2005 | Burwell et al. | 600/408 |

* cited by examiner

*Primary Examiner* — Eric F Winakur
*Assistant Examiner* — Hien Nguyen
(74) *Attorney, Agent, or Firm* — Hasse & Nesbitt LLC; Daniel F. Nesbitt

(57) ABSTRACT

A multi-layered structure in the form of a disposable patch is described for supporting a light source and useful in conjunction with procedures for the non-invasive visualization of veins, arteries or other subcutaneous structures of the body or for facilitating intravenous insertion or extraction of fluids, medication or the like, which in a representative embodiment includes a coupling layer for interfacing and optically coupling with the body surface and conforming to the surface topography of the body portion of interest, a ring for supporting a light source, and a reflective layer between the source and coupling layer for redirecting light reflected from the body surface back through the coupling layer.

21 Claims, 1 Drawing Sheet

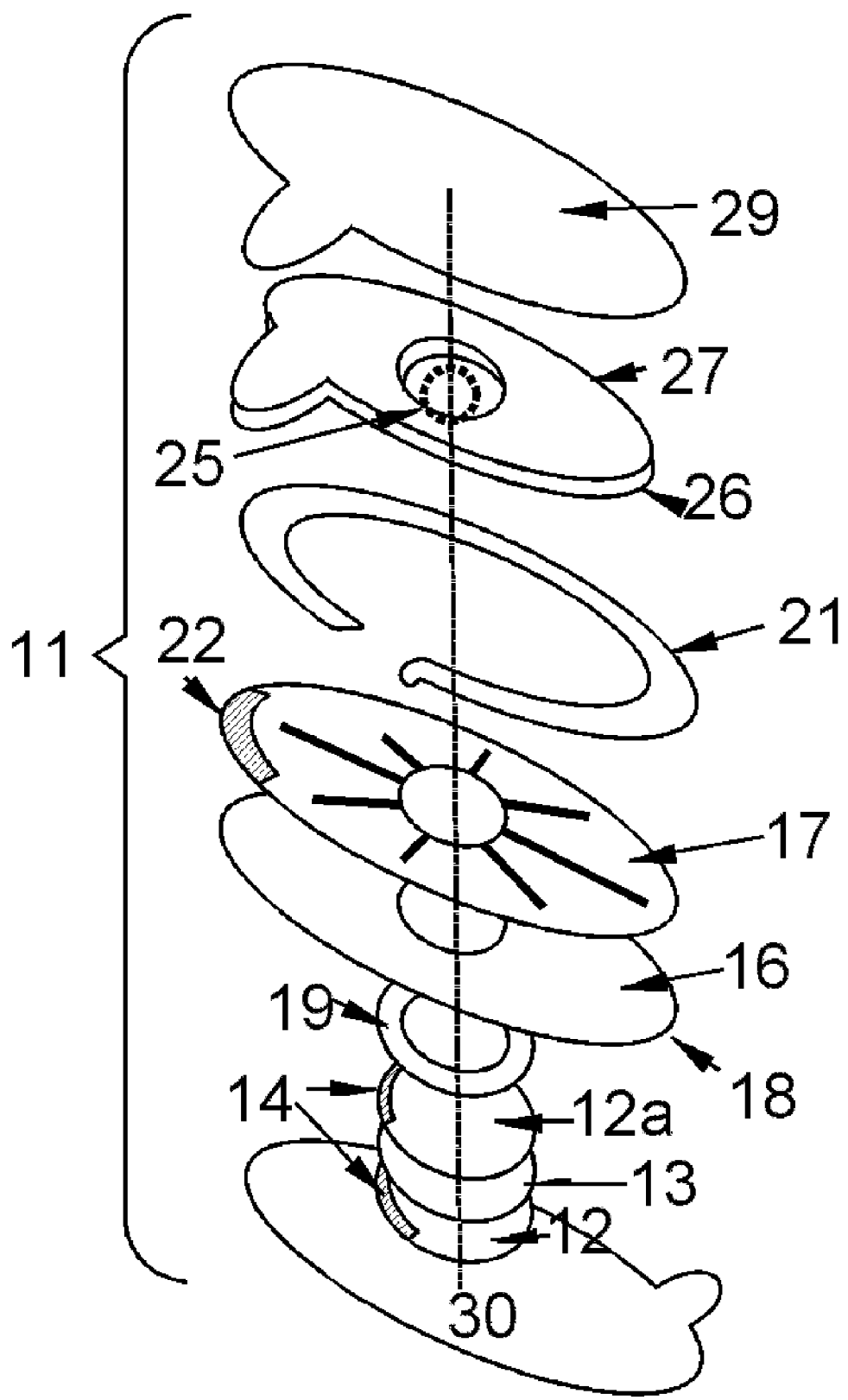

DISPOSABLE LIGHT SOURCE PATCH FOR ENHANCED VISUALIZATION OF SUBCUTANEOUS STRUCTURES

CROSS REFERENCE TO RELATED APPLICATION

This application claims the benefit of U.S. Provisional Application No. 60/680,600 filed May 13, 2005.

RIGHTS OF THE GOVERNMENT

The invention described herein may be manufactured and used by or for the Government of the United States for all governmental purposes without the payment of any royalty.

BACKGROUND OF THE INVENTION

The present invention relates generally to medical devices and procedures, and more particularly to a disposable housing structure in the form of an adhesive patch structure for supporting a light source, such as an infrared light source, useful in conjunction with systems and methods for enhancing visualization of veins, arteries and other subcutaneous structures of the body in the administration of medical treatment to a patient.

In the administration of medical care of a patient requiring vascular access, especially in an emergency situation, such as that encountered by a physician, nurse, emergency medical technician (EMT), or other health care provider, in the treatment of an accident victim at the scene of the accident, or by a medic in the treatment of the wounded on a battlefield, the conditions under which the care is administered may be adverse, such as nighttime lighting conditions. It is well settled that expeditious administration of medical care to the victim improves the prospects of recovery of the victim. For example, the life of a wounded soldier on the battlefield may depend on the immediate intravenous administration of blood plasma or other lost body fluids or of medications. Similar immediate procedures by a physician or EMT may be required in order to treat a victim at the scene of an accident. Further, during transport of the victim to a hospital or similar medical care facility, administration of medical procedures may be necessary under poor lighting conditions or under other adverse conditions (e.g., torn clothing, bleeding, etc) consequent of the accident. Shock may have caused the veins of the victim to partially collapse, or the patient may have veins which are difficult to find (such as in the treatment of infants or obese persons) which further complicates procedures for gaining access to the veins. The treatment of patients requiring vascular access in non-emergency situations may also be complicated by patient size, obesity, skin pigmentation or other physical characteristic.

In the practice of the procedures for visualization of subcutaneous structures using either visible, infrared or near infrared light, proper support of the light source in order to accurately direct the light onto a body portion of interest may be an awkward procedure for the health care provider in treating a patient. There is therefore indicated a need for a hands-free device for supporting the light source and directing light from the source onto the body portion of interest in the imaging process.

SUMMARY OF THE INVENTION

A multi-layered structure in the form of a disposable patch is described for supporting a light source and useful in conjunction with procedures for the non-invasive visualization of veins, arteries or other subcutaneous structures of the body or for facilitating intravenous insertion or extraction of fluids, medication or the like, which in a representative embodiment includes a coupling layer for interfacing and optically coupling with the body surface and conforming to the surface topography of the body portion of interest, a ring for supporting a light source, and a reflective layer between the source and coupling layer for redirecting light reflected from the body or scattered by the subcutaneous structures back through the coupling layer into the body surface under examination.

The invention is particularly useful in conjunction with systems and methods for the detection and display of subcutaneous structures such as described in U.S. Pat. No. 6,230,046 to Crane et al, which describes system and method for enhancing the visualization of veins, arteries or other subcutaneous natural or foreign structures in the body and for facilitating intravenous insertion or extraction of fluids, medications or the like in the administration of medical treatment to a patient, including a light source of selected wavelength(s) for illuminating or transilluminating a selected portion of the body and a low-level light detector and suitable filters for generating an image of the illuminated body portion. Substantial background material useful in the understanding of the invention may be found by reference to U.S. Pat. No. 6,230,046 and to Publication Number US 2004/0215081.

It is therefore a principal object of the invention to provide a housing structure for supporting a light source useful in the real-time, non-invasive visualization or identification of subcutaneous structures of the body.

It is another object of the invention to provide a patch structure for supporting the light source in a hands free manner.

It is yet another object of the invention to provide a patch structure adhesively attachable to a body portion of a patient.

It is another object of the invention to provide a patch structure that can be applied to a body portion of the patient in close conformance to the topography of complex surface features of the body.

It is yet another object of the invention to provide a patch structure that couples optically with the surface of the body portion of a patient in illuminating the body portion with light of selected wavelength.

It is yet another object of the invention to provide a patch structure for use in medical imaging procedures that useful in scanning the surface of the body under examination with near infrared light in order to choose an optimum illumination position for the light source.

These and other objects of the invention will become apparent as a detailed description of representative embodiments thereof proceeds.

BRIEF DESCRIPTION OF THE DRAWINGS

The invention will be more clearly understood from the following detailed description of representative embodiments thereof read in conjunction with the accompanying drawing figure that shows an exploded view of a representative embodiment of the patch structure of the invention.

DETAILED DESCRIPTION OF THE INVENTION

Referring now to the accompanying drawing figure, shown therein in an exploded view are the essential elements of a patch 11 structure representative of the invention along with the supporting structural elements that render the structure a complete unit. In accordance with a principal feature of the invention, patch 11 is configured to facilitate the illumination of a body portion of a patient with visible (V), infrared (IR) or near infrared (nIR) light in the practice of a process for visualization of subcutaneous structures in the body. A first substantially optically transparent layer 12 is configured to interface with the surface of the body portion of interest to be illuminated. For the purpose of describing the invention and defining the scope thereof, the terms "optical" or "optically" shall, in accordance with customary usage, be defined to include the ultraviolet, visible, nIR and IR regions of the electromagnetic spectrum lying between about 0.1 to about 1500 microns.

In order to minimize reflections at the interface and to efficiently illuminate the body surface with the available light from a suitable light source that is used in conjunction with the invention, the refractive index of layer 12 should be closely matched to the refractive index of the body portion of interest. The refractive index to infrared light of skin and tissue of the body is generally about 1.3 to 1.6. Accordingly, in contemplation of the invention, efficient coupling would result for a refractive index of layer 12 in the range of about 1.33 to 1.55. In order to efficiently couple light into the body surface, layer 12 should make substantially intimate laminar contact with the body surface in order to conform to various complex surface features of the skin, such as moles or hair, or various skin conditions such as acne, psoriasis, lesions, or other blemishes that would result in pockets or gaps of air in the interface that inhibit optical coupling with the body surface, and result in Fresnel reflections at the interface. Layer 12 should also provide a layer of thermal insulation between the light source and the surface of the skin so as to prevent discomfort to the patient or thermal damage to the skin, and to provide a sterile barrier between the light source should the patch or source need to be paced near or across a wound. Materials comprising layer 12 useful in the structure of patch 11 as an optical coupling layer and as a thermal diffuser include polyurethane, polyethylene, poly methacrylate, polyester, polydimethylsiloxane, a hydrocolloid gel or other highly transmissive, conformable material. Other materials may be selected by one skilled in the art guided by these teachings without departing from the spirit of the invention of the scope of the appended claims, material selection therefore not considered limiting of the invention herein. In the representative structure shown in the drawing that was built in demonstration of the invention, layer 12 comprised a thin layer (20 to 80 mils thick, preferably 30-50 mils) (1 mil=0.001 inch) of a hydrogel (such as Tegaderm™) as having good thermal insulative properties, good refractive match of approximately 1.33, and conforms well with the body surface contours. In the demonstration structure, layer 12 was about 41 mils thick and supported by a thin 1 mil thick film 13 of an IR transparent polymer having a suitable refractive index in the range of about 1.35 to 1.5, such polyethylene or polyurethane or other suitable elastomeric material such as polydimethylsiloxane, to protect layer 12 from tearing during use of the patch. Layer 12 may include an optional ring 14 of an IR opaque dye (e.g., Epolight™ 1175 or 1130 or ADS900AF) in order to prevent light scattering beyond the edges of coupling layer 12.

Structural support for layer 12 is provided by a pair of thin layer 16 (0.1 to 1 mil) and layer 17 (0.5 to 2 mils) of a structural polymer, such as polyethylene, polyurethane, polyethylene terephthalate (PET), polyethylene or polyurethane, each having a central opening for passing light through the structure to illuminate the body surface through layer 12. Layer 16 is comprised of a high toughness, low strain to failure polymeric material to prevent the premature fracture or tearing of the thin reflective aluminum film described below in order to prevent leakage of light from layer 12 back through layers 16, 17. Additionally, layers 16, 17 provide some structural rigidity to the overall structure of patch 11 while permitting layer 12 to conform to the body surface contour as just described.

A reflective film can be included in the structure in order to direct back through coupling layer 12 light that might be reflected from the body surface at the coupling layer/body surface interface or from the subcutaneous structures being observed. In the structure of the embodiment shown in the drawing and built in demonstration of the invention, a reflective aluminum film 18 was supported on the underside of layer 16 for directing back through layer 12 light that is backscattered from the interface with the body surface. Aluminum film 18 also serve as a conductor of heat away from the light source. A special adhesive layer comprising ring 19 (such as Entrofilm 892 used in demonstration of the invention) provides adhesion between layer 13 supporting the hydrogel coupling layer and the reflective aluminum layer 18. Structural support ring 21 (2 to 6 mils thick) of a synthetic polymeric or natural material was applied to polymer layer 17 for additional structural support. This support ring 21 permits the removal of layers 29 and 30 (described below) without wrinkling the other layers of the patch structure, thereby providing structural support for the patch after layers 29, 30 are removed when the patch is used as intended. Layer 17 may include high refractive index lines printed thereon to conduct light to the light source, which may contain circuits that control the light output of the source for optimum imaging; these lines may also be used to detect backscattered light to indicate presence of tissue or contact with the body surface as a safety feature against inadvertent heating of the body surface. The paths are high index lines (shown in the drawing as radially extending lines on layer 17) that are formed in the polymeric portion of layer 16 to provide light intensity values at various places of the patch/skin interface. It should be noted that the aluminum film may also be used to detect the presence of tissue via a change in capacitance caused by the presence with the intervening dielectric materials.

A visible (V), IR or nIR light source 25 (such as one or more light emitting diodes, a chemiluminescent source or other suitable source, shown by dashed lines) may be inserted into and supported within two rings 26, 27 of foam, such as polyethylene foam and connected to a suitable source of power (not shown) for illumination of the body surface area of interest in accordance with the intended use of the invention. In an aspect of the invention contemplated herein, the light source 25 can include a disposable source, such as including a battery powered LED, for field or emergency usage. Foam layer 26 (abut 20 to 80 mils thick) provides primary support for the light source and may preferably comprise carbon filed polyethylene foam to prevent light leaks from the source. Foam layer 27 (about 0.5 to 4 mils thick) controls the adhesion of the two layer structure specifically to prevent layer 26 from sticking to the light source and to release the source when use of the patch is complete. As such, layer 27 must have a specific adhesion and thermal capabilities. The adhesion values of between 2 and 10 pound/linear inch with a value between 4 and 6 pound/linear inch peel will provide a suitable adhesion in contemplation of the invention. A protective pull-tab 29 comprising a protective contaminant barrier layer (1 to 5 mils thick, preferably 2 to 4 mils) of polyester or other suitable material is removed and discarded prior to attachment of source 25. A second protective contaminant barrier layer 30 of a polymer (1 to 7 mils thick, preferably 2 to 4 mils) covers the under surface of patch 11 at layer 12 and is removed and discarded prior to the application of patch 11 to the skin of the subject. Layers 29, 30 should be nIR transparent with low scattering. In the demonstration embodiment, layers 29, 30 were each 3 mils thick. Prior to the removal of protective layer 30, the patch structure may be used in a scanning mode to determine the optimum location for illuminating the intended cannulation site for placement of the patch in an imaging procedure.

The patch structure according to the teachings of the invention may be of any convenient size consistent with the size of the person on which the patch is used, and thicknesses of the individual layers comprising the patch structure may be selected by the skilled artisan practicing the invention within the intended scope of these teachings, the thicknesses hereinabove recited as included in demonstration of the invention being representative only. It is noted further that the invention may find use in veterinary medicine as well as for human application. In the demonstration embodiment, overall size of the patch was about 2 to 6 inches in diameter and about 0.170 inch in overall thickness for use on an adult person. Minimum size of the patch may be limited by the size of the light source selected for use in conjunction with the patch and by the size of the body features of infant patients.

The entire teachings of all references cited herein are incorporated herein by reference.

The invention therefore provides a disposable patch structure for supporting a light source having particular application in systems and methods for enhanced visualization of subcutaneous structures. It is understood that modifications to the invention may be made as might occur to one with skill in the field of the invention within the scope of the appended claims. All embodiments contemplated hereunder that achieve the objects of the invention have therefore not been shown in complete detail. Other embodiments may be developed without departing from the spirit of the invention or from the scope of the appended claims.

We claim:

1. A patch structure for use in medical imaging procedures, comprising:
    a first layer comprising optically transparent conformable material consisting of hydrogel, having a bottom surface that is configured to conform to a body surface of a patient to establish intimate laminar contact with the body surface, for optically coupling the first layer to the body surface of the patient at an interface between the bottom surface of the first layer and the body surface;
    a second layer comprising an optically transparent polymer or elastomer, said second layer supporting the first layer;
    a light source comprising a light emitting diode (LED) that emits infrared (IR) or near infrared (nIR) light through the optically transparent polymer or elastomer of the second layer and the transparent conformable hydrogel material of the first layer, to illuminate subcutaneous structures body below the body surface;
    a third layer for supporting the light source; and
    a reflective surface having an aperture through which the emitted light passes, the reflective surface disposed between the first layer and the third layer for reflecting light reflected from the body surface back through the first layer to the interface.

2. The patch structure of claim 1 wherein said reflective surface comprises an aluminum film on a layer of polymer disposed between said first layer and said third layer.

3. The patch structure of claim 1 wherein the index of refraction of said first layer is in the range of about 1.33 to about 1.55.

4. The patch structure of claim 1 wherein the index of refraction of said second layer is in the range of about 1.35 to about 1.5.

5. The patch structure of claim 1 wherein said second layer comprises polyethylene or polyurethane.

6. The patch structure of claim 1 wherein said first layer is thermally insulative.

7. The patch structure of claim 1 wherein said third layer is a foam.

8. The patch structure of claim 7 further comprising removable first and second contaminant barrier layers respectively on said bottom surface of said first layer and on said foam layer.

9. The patch structure of claim 1 further comprising an optically transparent structural polymer layer disposed between and optically coupling the second layer and the third layer.

10. The patch structure of claim 1 wherein the light source is a battery-powered LED light source.

11. A patch structure for use in medical imaging procedures, comprising:
    a first layer comprising optically transparent conformable material said first layer having a bottom surface that is configured to conform to a body surface of a patient to establish intimate laminar contact with the body surface, for optically coupling the first layer to the body surface of the patient at an interface between the bottom surface of said first layer and the body surface;
    a second layer comprising an optically transparent polymer or elastomer, said second layer supporting said first layer and attached to a top surface opposite the bottom surface of the first layer;
    a third layer for supporting a light source;
    a reflective surface having an aperture through which the emitted light passes, the reflective surface disposed between said second layer and said third layer for reflecting light from the body surface back through said first layer to the interface;
    an adhesive layer interfacing said second layer and said reflective surface; and
    an optically transparent structural polymer layer for optically coupling said first layer with the source of light.

12. The patch structure of claim 11 wherein said reflective surface comprises an aluminum film on a layer of polymer disposed between said first layer and said third layer.

13. The patch structure of claim 11 wherein the index of refraction of said first layer is in the range of about 1.33 to about 1.55.

14. The patch structure of claim 11 wherein the index of refraction of said second layer is in the range of about 1.35 to about 1.5.

15. The patch structure of claim 11 wherein said second layer comprises polyethylene or polyurethane.

16. The patch structure of claim 11 wherein said first layer is a hydrogel.

17. The patch structure of claim 11 where said first layer comprises a material selected from the group consisting of polyurethane, polyethylene, poly methacrylate, polyester, and polydimethylsiloxane.

18. The patch structure of claim 11 wherein said third layer is a foam.

19. The patch structure of claim 18 further comprising removable first and second contaminant barrier layers respectively on said bottom surface of said first layer and on said foam layer.

20. The patch structure of claim 11 further comprising a light source.

21. The patch structure of claim 20 wherein the light source is a battery-powered LED light source.

* * * * *